Feb. 4, 1964 C. FISCHER Plant Pat. 2,354
GLADIOLUS PLANT
Filed Sept. 18, 1962
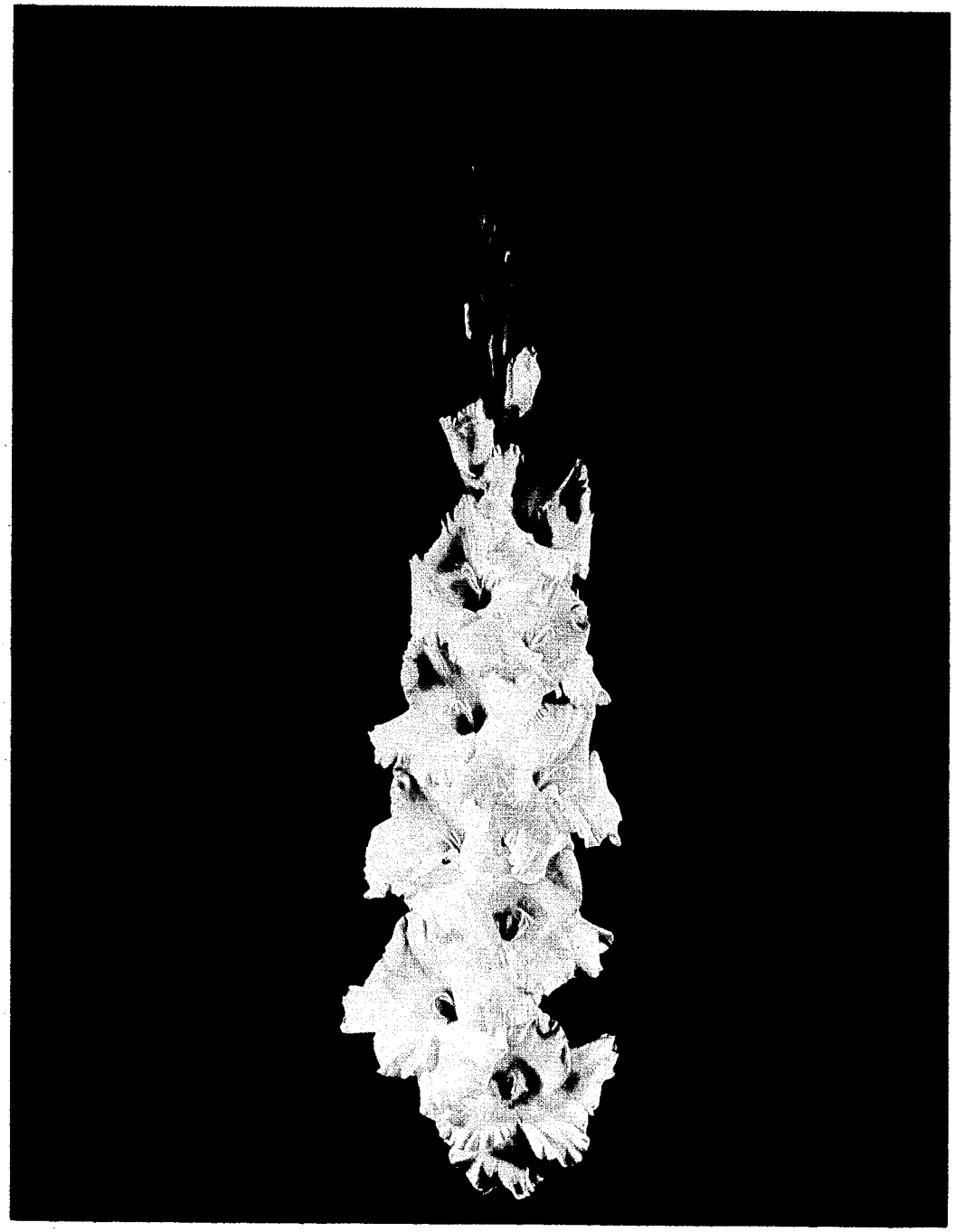
Inventor.
Carl Fischer
By: Robb & Robb
Attorneys.

United States Patent Office

Plant Pat. 2,354
Patented Feb. 4, 1964

2,354
GLADIOLUS PLANT

Carl Fischer, St. Charles, Minn., assignor to Imperial Flowers Limited, Leamington, Ontario, Canada, a corporation of Canada Filed Sept. 18, 1962, Ser. No. 224,583
1 Claim. (Cl. Plt.—35)

The present invention relates to a new and distinct variety of gladiolus plant which was originated by me by crossing the variety known as "Campanile" (unpatented) with the variety known as "Innocence" (unpatented), the former being the seed parent, and the latter being the pollen parent.

The foregoing breeding was performed by me by manual cross pollination in the course of my breeding of new gladiolus varieties in my outdoor breeding fields at St. Charles, Minnesota. The primary objective of this particular cross was to obtain a new gladiolus variety which is characterized by good flower productivity, an early blooming habit and production of snowy white flowers. This objective was fully achieved, along with other desirable features, as evidenced by the following combination of unique characteristics which are outstanding in the new variety and which distinguish it from its parents, as well as from all other varieties of which I am aware:

(1) A healthy habit of growth;
(2) An early blooming habit;
(3) Good productivity; and
(4) A distinctive and attractive snow white general color tonality of the flowers.

My new variety resembles the variety known as "June Wedding" (unpatented) more than any other, but differs principally therefrom by having a taller and more formal habit of growth; greater productivity, as evidenced by the production of more flower spikes per bulb; and a distinctive and unusual bud sheath which flares out at a sharp angle at the tip thereof.

Asexual reproduction of my new variety by cormels through several generations, as performed by me at St. Charles, Minnesota, shows that the foregoing characteristics and distinctions come true to form and are established and transmitted through succeeding propagations.

The accompanying drawing shows a typical specimen flower spike of my new variety, with the flowers in different stages of development ranging from closed buds through partially open buds to fully open flowers, as depicted in color as nearly true as it is reasonably possible to make the same in a color illustration of this character.

The following is a detailed description of my new variety, with color terminology in accordance with the Horticultural Colour Charts issued by the British Colour Council and the Royal Horticultural Society, except where general color terms of ordinary dictionary significance are obvious:

Locality where grown and observed: St. Charles, Minnesota.

Propagation: Holds its distinguishing characteristics through succeeding propagations by plantings derived from cormels.

*Plant*

Growth: Prolific propagator; ranges from 60 inches to 62 inches in height.

Blooming habit: A very early bloomer in the Northern latitudes of the United States; comes into bloom from large bulbs in about 65 days.

Stems: Willowy.

*Diameter at base.*—From about ⅜ inch to about ½ inch.

*Color (just above the bulb).*—Mallow Purple, Plate 630/1.

Foliage: Leaves generally upright, but outer leaves droop slightly and leaves usually have a slight twist; leaves range about 1¼ inches to 1½ inches wide; attain height of about 40 inches. Color—deep green.

Disease resistance: Unusually good resistance to Fusarium yellows, Sclerotina dry rot and Septoria leaf spot, as determined by comparison with other varieties grown in my fields near St. Charles, Minnesota, in irrigated black loam soil.

Corms (bulbs): Healthy; round; rough-looking; extremely vigorous; average about 2 inches in diameter. Color of flesh—Empire Yellow, Plate 603/3.

*Flower*

Spike: Tall; bears from 18 to 20 buds, with 9 florets usually opening at once, and 5 or 6 buds showing color; flower head ranges from about 24 inches to 26 inches long.

Bud:

*Size.*—From about 2½ inches to 3 inches long when opening.

*Opening.*—5 or 6 buds show color at one time; opens well.

Flower:

*Arrangement.*—Florets are semi-formally arranged in a double row on the stem and usually all face forward.

*Size.*—Lower florets average about 5 inches in diameter, with upper florets being progressively smaller.

*Form.*—Very round; recurved; ruffled; semi-formal arrangement; individual florets face somewhat upward.

*Keeping qualities.*—Keeps well.

Petals:

*Shape.*—Round; ruffled; recurved; flat-open.

*Size.*—Outer petals—from 2¼ inches to 2½ inches wide. Lip petal—1½ inches wide.

*Aspect.*—Heavy substance; smooth surface.

*Fragrance.*—None.

*Color.*—Opening buds are Uranium Green, Plate 63/3, with faint line of Phlox Pink, Plate 625/2 where petals emerge from calyx; colors change to snowy white in open flowers.

*Reproductive Organs*

Stamens: Color—cream, with tint of light rose.

Pistil: Color—white.

I claim:

A new and distinct variety of gladiolus plant, substantially as herein shown and described, characterized particularly as to novelty by the unique combination of a healthy habit of growth, an early blooming habit, good flower productivity, and a distinctive and attractive snowy white general color tonality of the open flowers.

No references cited.